United States Patent
Scott et al.

(10) Patent No.: US 10,732,301 B2
(45) Date of Patent: Aug. 4, 2020

(54) BEAM DETECTION AND FILTERING NOISE

(71) Applicant: CARESTREAM HEALTH, INC., Rochester, NY (US)

(72) Inventors: Richard T. Scott, Hilton, NY (US); Eric M. Welch, Avon, NY (US); Karin Toepfer, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 16/309,509

(22) PCT Filed: Jun. 26, 2017

(86) PCT No.: PCT/US2017/039178
§ 371 (c)(1),
(2) Date: Dec. 13, 2018

(87) PCT Pub. No.: WO2018/005309
PCT Pub. Date: Jan. 4, 2018

(65) Prior Publication Data
US 2019/0310382 A1    Oct. 10, 2019

Related U.S. Application Data

(60) Provisional application No. 62/354,900, filed on Jun. 27, 2016.

(51) Int. Cl.
*G01T 1/166* (2006.01)
*A61B 6/00* (2006.01)

(52) U.S. Cl.
CPC .............. *G01T 1/1663* (2013.01); *A61B 6/54* (2013.01); *A61B 6/42* (2013.01); *A61B 6/50* (2013.01)

(58) Field of Classification Search
CPC   G01T 1/1663; A61B 6/54; A61B 6/50; A61B 6/42
See application file for complete search history.

(56) References Cited

U.S. PATENT DOCUMENTS

| | | | |
|---|---|---|---|
| 2012/0273655 A1* | 11/2012 | Ise | H04N 5/361 250/208.1 |
| 2013/0320224 A1 | 12/2013 | Sato | |
| 2016/0103229 A1* | 4/2016 | Okada | G01T 1/17 378/62 |

OTHER PUBLICATIONS

International Search Report dated Sep. 15, 2017 for International Application No. PCT/US2017/039178, 2 pages.

* cited by examiner

*Primary Examiner* — David P Porta
*Assistant Examiner* — Meenakshi S Sahu

(57) ABSTRACT

A digital radiographic detector outputs positive read out signals that may oscillate. The presence of negative going portions of the read out signals may be used to determine that the detected positive signals are a result of noise, while an absence of the negative going portions may be used to determine that x-rays are impacting the detector.

19 Claims, 8 Drawing Sheets

| Strip Classification | | |
|---|---|---|
| +Threshold Condition | −Threshold Condition | Strip Classification |
| YES | YES | Noise |
| YES | NO | Beam On |
| NO | YES | Noise |
| NO | NO | Dark |

| Frame Classification | | |
|---|---|---|
| Strip Classification | Strip Classification | Frame Classification |
| Beam On | ignore | Beam Detect |
| Not Beam On | Noise | Noise |
| Dark | Dark | Dark |

| Current Frame Disposition | | |
|---|---|---|
| Prior Frame Classification | Current Frame Classification | Frame Disposition |
| Beam Detect | Beam Detect | Continue Radiographic Capture |
| Beam Detect | Not Beam Detect | End Radiographic Capture |
| Not Beam Detect | Beam Detect | Start Radiographic Capture |
| Not Beam Detect | Noise | Discard |
| Not Beam Detect | Dark | Capture Dark |

*FIG. 7*

BEAM DETECTION AND FILTERING NOISE

CROSS REFERENCE TO RELATED APPLICATIONS

This application claims the benefit of and is a U.S. National Phase filing of PCT Application PCT/US2017/039178 filed Jun. 26, 2017 entitled "BEAM DETECTION AND FILTERING NOISE", in the name of Scott et al., which claims benefit of U.S. Patent Application Ser. No. 62/354,900, filed Jun. 27, 2016, in the name of Scott et al., and entitled BEAM DETECT AND NOISE FILTER.

This application is related in certain respects to International Application WO 2016/094503 A1, filed Dec. 9, 2015, in the name of Topfer et al., and entitled BEAM DETECTION WITH CONTINUOUS DETECTOR READOUT, which is incorporated herein by reference in its entirety.

BACKGROUND OF THE INVENTION

The subject matter disclosed herein relates to digital radiographic detectors. In particular, to methods and apparatuses for determining a detection of a false x-ray beam start by detecting negative going signals.

BRIEF DESCRIPTION OF THE INVENTION

A digital radiographic detector outputs positive read out signals that may oscillate. The presence of negative going portions of the read out signals may be used to determine that the detected positive signals are a result of noise, while an absence of the negative going portions may be used to determine that x-rays are impacting the detector. An advantage that may be realized in the practice of some disclosed embodiments of the digital radiographic detector is filtering out false beam detection events.

In one embodiment, output signals of a digital radiographic detector are monitored. Positive signals in the output signals may be detected while negative signals are not detected. An algorithm is used to determine that the detected positive signals are a result of x-rays impacting the imaging pixels based on not detecting the negative signals.

In another embodiment, output signals of a digital radiographic detector are monitored. Positive signals in the output signals may be detected as well as negative signals. An algorithm is used to determine that the detected positive signals are not caused by x-rays impacting the imaging pixels in the detector based on detecting the negative signals.

In another embodiment, read out signals of a digital radiographic detector are monitored. Positive signals as well as negative signals in the read out signals may be absent for a full image frame of data. The full frame of image data is stored based on not detecting positive or negative signals.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 7 is an exemplary table illustrating application of an algorithm disclosed herein to classify strips and rows and to disposition image data frames.

DETAILED DESCRIPTION OF THE INVENTION

This application claims priority to U.S. Patent Application Ser. No. 62/354,900, filed Jun. 27, 2016, in the name of Scott et al., and entitled BEAM DETECT AND NOISE FILTER.

This application is related in certain respects to International Application WO 2016/094503 A1, filed Dec. 9, 2015, in the name of Topfer et al., and entitled BEAM DETECTION WITH CONTINUOUS DETECTOR READOUT, which is incorporated herein by reference in its entirety.

Figure 1:
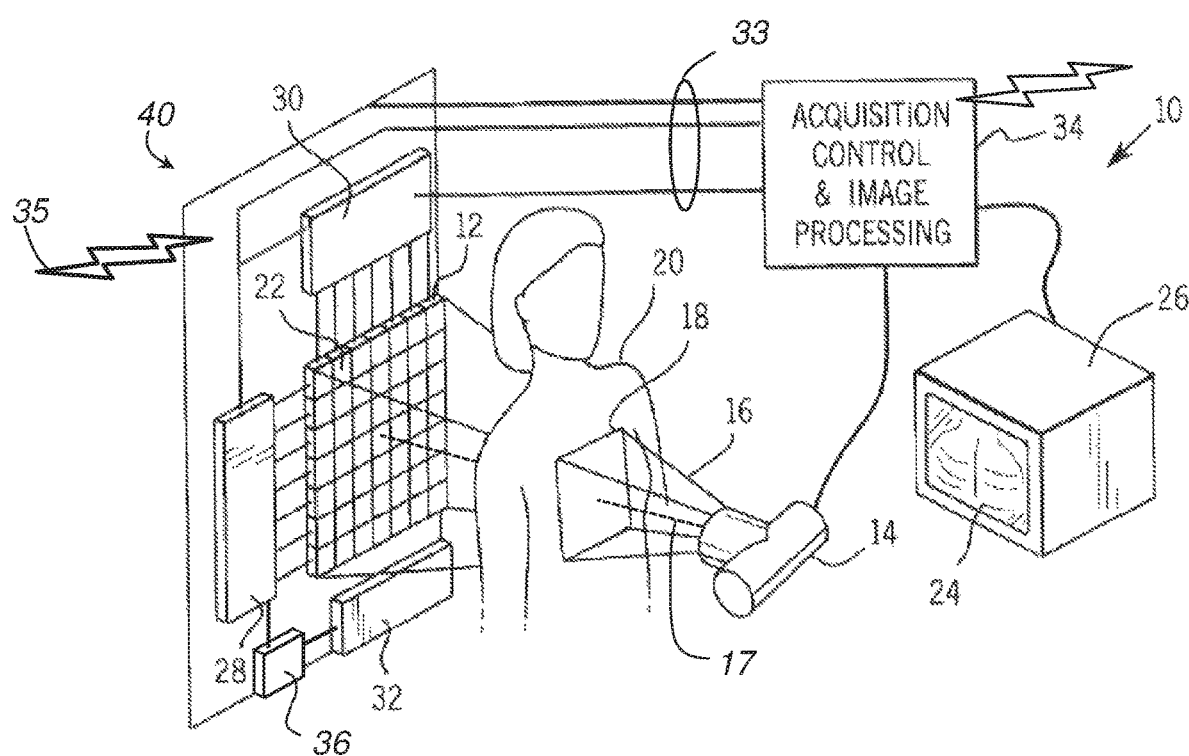
FIG. 1 is a schematic perspective view of an exemplary x-ray system.

FIG. 1 is a perspective view of a digital radiographic (DR) imaging system 10 that may include a generally curved or planar DR detector 40 (shown in a planar embodiment and without a housing for clarity of description), an x-ray source 14 configured to generate radiographic energy (x-ray radiation), and a digital monitor, or electronic display, 26 configured to display images captured by the DR detector 40, according to one embodiment. The DR detector 40 may include a two dimensional array 12 of detector cells 22 (photosensors), arranged in electronically addressable rows and columns. The DR detector 40 may be positioned to receive x-rays 16 passing through a subject 20 during a radiographic energy exposure, or radiographic energy pulse(s), emitted by the x-ray source 14. As shown in FIG. 1, the radiographic imaging system 10 may use an x-ray source 14 that emits collimated x-rays 16, e.g. an x-ray beam, selectively aimed at and passing through a preselected region 18 of the subject 20. The x-ray beam 16 may be attenuated by varying degrees along its plurality of rays according to the internal structure of the subject 20, which attenuated rays are detected by the two-dimensional array 12 of photosensitive detector cells 22. The curved or planar DR detector 40 is positioned, as much as possible, in a perpendicular relation to a substantially central ray 17 of the plurality of rays 16 emitted by the x-ray source 14. In a curved array embodiment, the source 14 may be centrally positioned such that a larger percentage, or all, of the photosensitive detector cells are positioned perpendicular to incoming x-rays from the centrally positioned source 14. The array 12 of individual photosensitive cells, imaging pixels, or photosensors 22 may be electronically addressed (scanned) by their position according to column and row. As used herein, the terms "column" and "row" refer to the vertical and horizontal arrangement of the photosensor cells 22 and, for clarity of description, it will be assumed that the rows extend horizontally and the columns extend vertically. However, the orientation of the columns and rows is arbitrary and does not limit the scope of any embodiments disclosed herein. Furthermore, the term "subject" may be illustrated as a human patient in the description of FIG. 1, however, a subject of a DR imaging system, as the term is used herein, may be a human, an animal, an inanimate object, or a portion thereof.

In one exemplary embodiment, the rows of photosensitive cells 22 may be scanned one or more at a time by electronic scanning circuit 28 so that the exposure data from the array 12 may be transmitted to electronic read-out circuit 30. Each photosensitive cell 22 may independently store a charge proportional to an intensity, or energy level, of the attenuated radiographic radiation, or x-rays, received and absorbed in the cell. Thus, each photosensitive cell, when read-out, provides information defining an imaging pixel of a radiographic image 24, e.g. a brightness level or an amount of energy absorbed by the imaging pixel, that may be digitally decoded by image processing electronics 34 and transmitted to the digital monitor 26 for display and for viewing by a user. In some embodiments, each row may be logically divided into a plurality of strips such that each strip, or section, of a row may be read, stored, processed, or a combination thereof, to determine an intensity and polarity of a signal detected therein. Such intensity determinations may be averaged and recorded per row, per strip, per plurality of rows and/or strips, or a combination thereof. An electronic bias circuit 32 may be electrically connected to the two-dimensional detector array 12 to provide a bias voltage to each of the photosensitive cells 22.

Each of the bias circuit 32, the scanning circuit 28, and the read-out circuit 30, may communicate with an acquisition control and image processing unit 34 over a connected cable 33 (wired), or the DR detector 40 and the acquisition control and image processing unit 34 may be equipped with a wireless transmitter and receiver to transmit radiographic image data wirelessly 35 to the acquisition control and image processing unit 34, or to transmit and receive program instructions or other commands. The acquisition control and image processing unit 34 may include a processor and electronic memory (not shown) to control operations of the DR detector 40 as described herein, including control of circuits 28, 30, and 32, for example, by use of programmed instructions, and to store and process image data. The acquisition control and image processing unit 34 may also be used to control activation of the x-ray source 14 during a radiographic exposure, controlling an x-ray tube electric current magnitude, and thus the fluence of x-rays in x-ray beam 16, and/or the x-ray tube voltage, and thus the energy level of the x-rays in x-ray beam 16. The acquisition control and image processing unit 34 may also receive instructions or commands transmitted from the DR detector 40.

A portion or all of the acquisition control and image processing unit 34 functions and hardware may reside in or be duplicated in the detector 40 in an on-board processing system 36 which may include a processor and electronic memory to control operations of the DR detector 40 as described herein, including control of circuits 28, 30, and 32, by use of programmed instructions, and to store and process image data similar to the functions of acquisition control and image processing system 34. The image processing system 36 may perform image acquisition and image disposition functions as described herein. The image processing system 36 may control image transmission and image processing and image correction on board the detector 40 based on instructions stored on-board processing system 36 or based on instructions or other commands transmitted from the acquisition control and image processing unit 34. The image processing system 36 may transmit corrected digital image data therefrom. Alternatively, acquisition control and image processing unit 34 may receive raw image data from the detector 40 and process the image data and store it, or it may store raw unprocessed image data in local memory, or in remotely accessible memory.

With regard to a direct detection embodiment of DR detector 40, the photosensitive cells 22 may each include a sensing element sensitive to x-rays, i.e. it absorbs x-rays and generates an amount of charge carriers in proportion to a magnitude of the absorbed x-ray energy. A switching element may be configured to be selectively activated to read out the charge level of a corresponding x-ray sensing element. With regard to an indirect detection embodiment of DR detector 40, photosensitive cells 22 may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, may be disposed over the light sensitive sensing elements to convert incident x-ray radiographic energy to visible light energy. Thus, in the embodiments disclosed herein, it should be noted that the DR detector 40 (or DR detector 300 in FIG. 3 or DR detector 400 in FIG. 4) may include an indirect or direct type of DR detector.

Examples of sensing elements used in sensing array 12 include various types of photoelectric conversion devices (e.g., photosensors) such as photodiodes (P-N or PIN diodes), photo-capacitors (MIS), photo-transistors or photoconductors. Examples of switching elements used for signal read-out include a-Si TFTs, oxide TFTs, MOS transistors, bipolar transistors and other p-n junction components.

Figure 2:
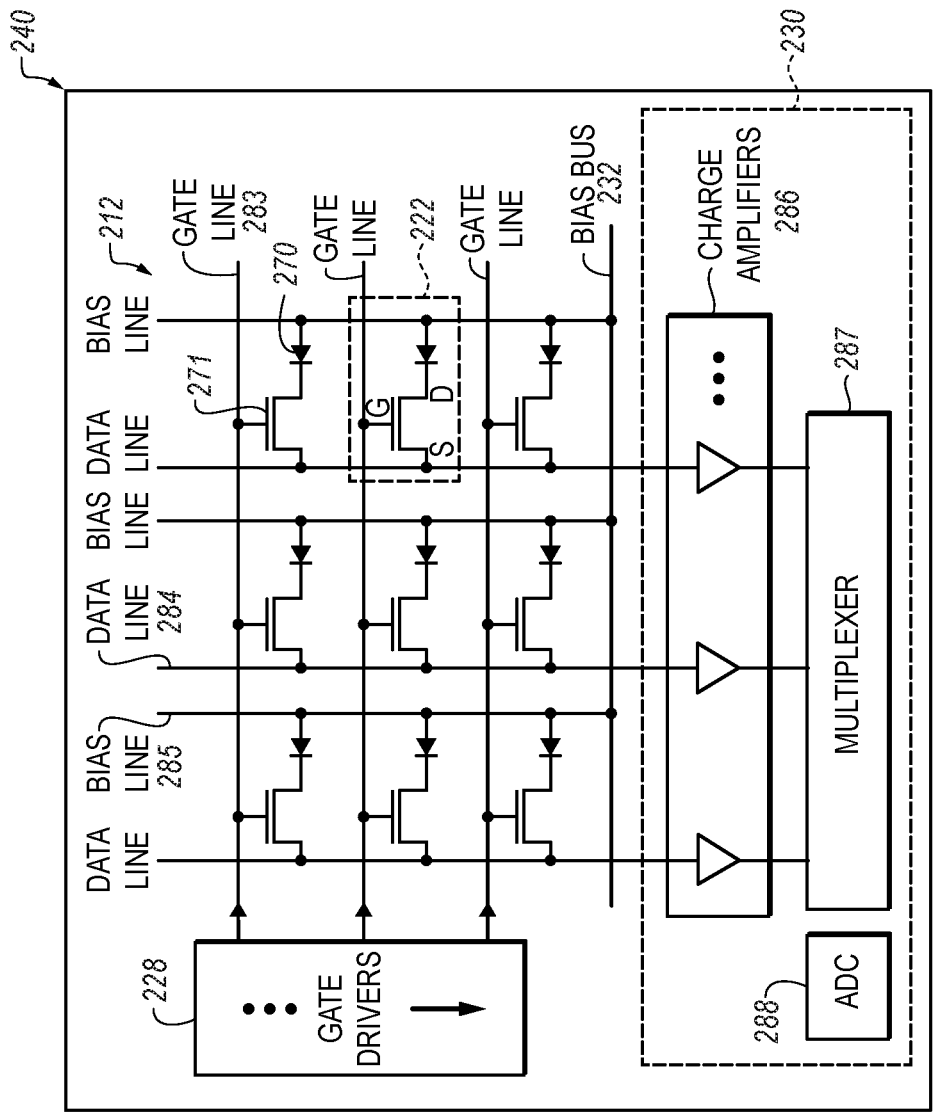
FIG. 2 is a schematic diagram of a photosensor array, or imaging pixel array, in an exemplary digital radiographic (DR) detector.

FIG. 2 is a schematic diagram 240 of a portion of a two-dimensional array 12 for a DR detector 40. The array of photosensor cells 212, whose operation may be consistent with the photosensor array 12 described above, may include a number of hydrogenated amorphous silicon (a-Si:H) n-i-p photodiodes 270 and thin film transistors (TFTs) 271 formed as field effect transistors (FETs) each having gate (G), source (S), and drain (D) terminals. In embodiments of DR detector 40 disclosed herein, such as a multilayer DR detector (400 of FIG. 4), the two-dimensional array of photosensor cells 12 may be formed in a device layer that abuts adjacent layers of the DR detector structure, which adjacent layers may include a rigid glass layer or a flexible polyimide layer without any adjacent rigid layers. A plurality of gate driver circuits 228 may be electrically connected to a plurality of gate lines 283 which control a voltage applied to the gates of TFTs 271, a plurality of readout circuits 230 may be electrically connected to data lines 284, and a plurality of bias lines 285 may be electrically connected to a bias line bus or a variable bias reference voltage line 232 which controls a voltage applied to the photodiodes 270. Charge amplifiers 286 may be electrically connected to the data lines 284 to receive signals therefrom. Outputs from the charge amplifiers 286 may be electrically connected to a multiplexer 287, such as an analog multiplexer, then to an analog-to-digital converter (ADC) 288, or they may be directly connected to the ADC, to stream out the digital radiographic image data at desired rates. In one embodiment, the schematic diagram of FIG. 2 may represent a portion of a DR detector 40 such as an a-Si:H based indirect flat panel, curved panel, or flexible panel imager.

Incident x-rays, or x-ray photons, 16 are converted to optical photons, or light rays, by a scintillator, which light rays are subsequently converted to electron-hole pairs, or charges, upon impacting the a-Si:H n-i-p photodiodes 270. In one embodiment, an exemplary detector cell 222, which may be equivalently referred to herein as a pixel, may include a photodiode 270 having its anode electrically connected to a bias line 285 and its cathode electrically connected to the drain (D) of TFT 271. The bias reference voltage line 232 can control a bias voltage of the photodiodes 270 at each of the detector cells 222. The charge capacity of each of the photodiodes 270 is a function of its bias voltage and its capacitance. In general, a reverse bias voltage, e.g. a negative voltage, may be applied to the bias lines 285 to create an electric field (and hence a depletion region) across the pn junction of each of the photodiodes 270 to enhance its collection efficiency for the charges generated by incident light rays. The image signal represented by the array of photosensor cells 212 may be integrated by the photodiodes while their associated TFTs 271 are held in a non-conducting (off) state, for example, by maintaining the gate lines 283 at a negative voltage via the gate driver circuits 228. The photosensor cell array 212 may be read out by sequentially switching rows of the TFTs 271 to a conducting (on) state by means of the gate driver circuits 228. When a row of the pixels 22 is switched to a conducting state, for example by applying a positive voltage to the corresponding gate line 283, collected charge from the photodiode in those pixels may be transferred along data lines 284 and integrated by the external charge amplifier circuits 286. The row may then be switched back to a non-conducting state, and the process is repeated for each row until the entire array of photosensor cells 212 has been read out. The integrated signal outputs are transferred from the external charge amplifiers 286 to an analog-to-digital converter (ADC) 288 using a parallel-to-serial converter, such as multiplexer 287, which together comprise read-out circuit 230.

This digital image information may be subsequently processed by image processing system 34 or 36 to yield a digital image which may then be digitally stored, transmitted, or immediately displayed on monitor 26, or it may be displayed at a later time by accessing digital electronic on-board memory, memory in the acquisition control & image processing 34, or remote memory such as in a network storage location containing the stored image. The flat panel DR detector 40 having an imaging array as described with reference to FIG. 2 is capable of both single-shot (e.g., static, radiographic) and continuous (e.g., fluoroscopic) image acquisition.

Figure 3:
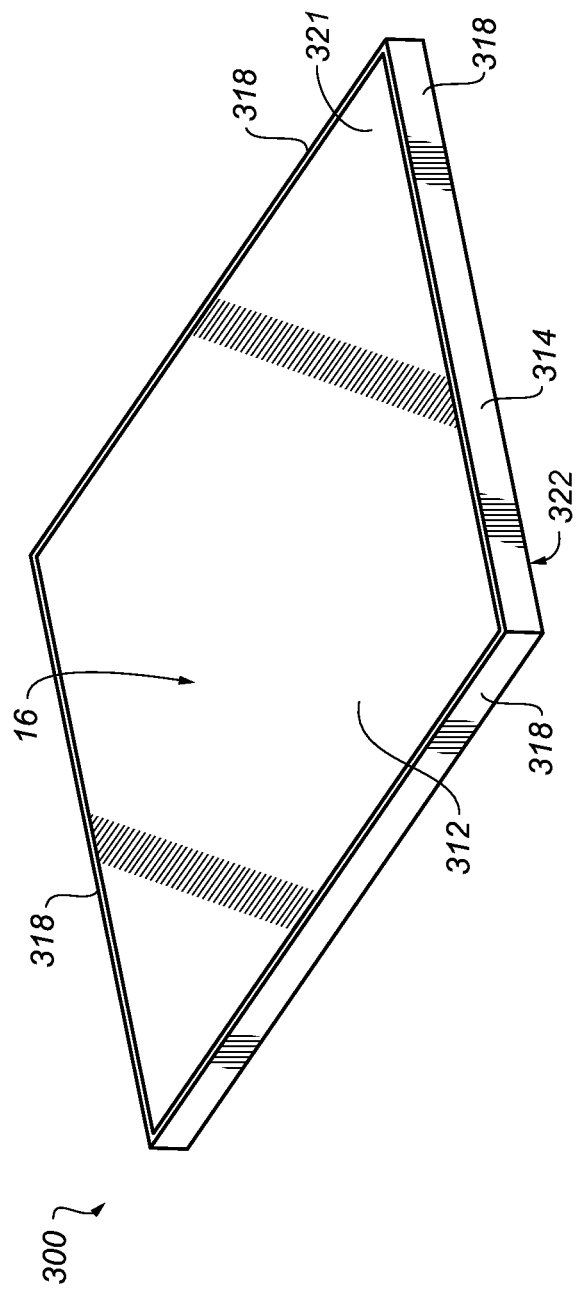
FIG. 3 is an exemplary diagram of a DR detector.

FIG. 3 shows a perspective view of an exemplary prior art generally rectangular, planar, portable wireless DR detector 300 according to an embodiment of DR detector 40 disclosed herein. The DR detector 300 may include a flexible substrate to allow the DR detector to capture radiographic images in a curved orientation. The flexible substrate may be fabricated in a permanent curved orientation, or it may remain flexible throughout its life to provide an adjustable curvature in two or three dimensions, as desired. The DR detector 300 may include a similarly flexible housing portion 314 that surrounds a multilayer structure comprising a flexible photosensor array portion 22 of the DR detector 300. The housing portion 314 of the DR detector 300 may include a continuous, rigid or flexible, x-ray opaque material or, as used synonymously herein a radio-opaque material, surrounding an interior volume of the DR detector 300. The housing portion 314 may include four flexible edges 318, extending between the top side 321 and the bottom side 322, and arranged substantially orthogonally in relation to the top and bottom sides 321, 322. The bottom side 322 may be continuous with the four edges and disposed opposite the top side 321 of the DR detector 300. The top side 321 comprises a top cover 312 attached to the housing portion 314 which, together with the housing portion 314, substantially encloses the multilayer structure in the interior volume of the DR detector 300. The top cover 312 may be attached to the housing 314 to form a seal therebetween, and be made of a material that passes x-rays 16 without significant attenuation thereof, i.e., an x-ray transmissive material or, as used synonymously herein, a radiolucent material, such as a carbon fiber plastic, polymeric, or other plastic based material.

Figure 4:
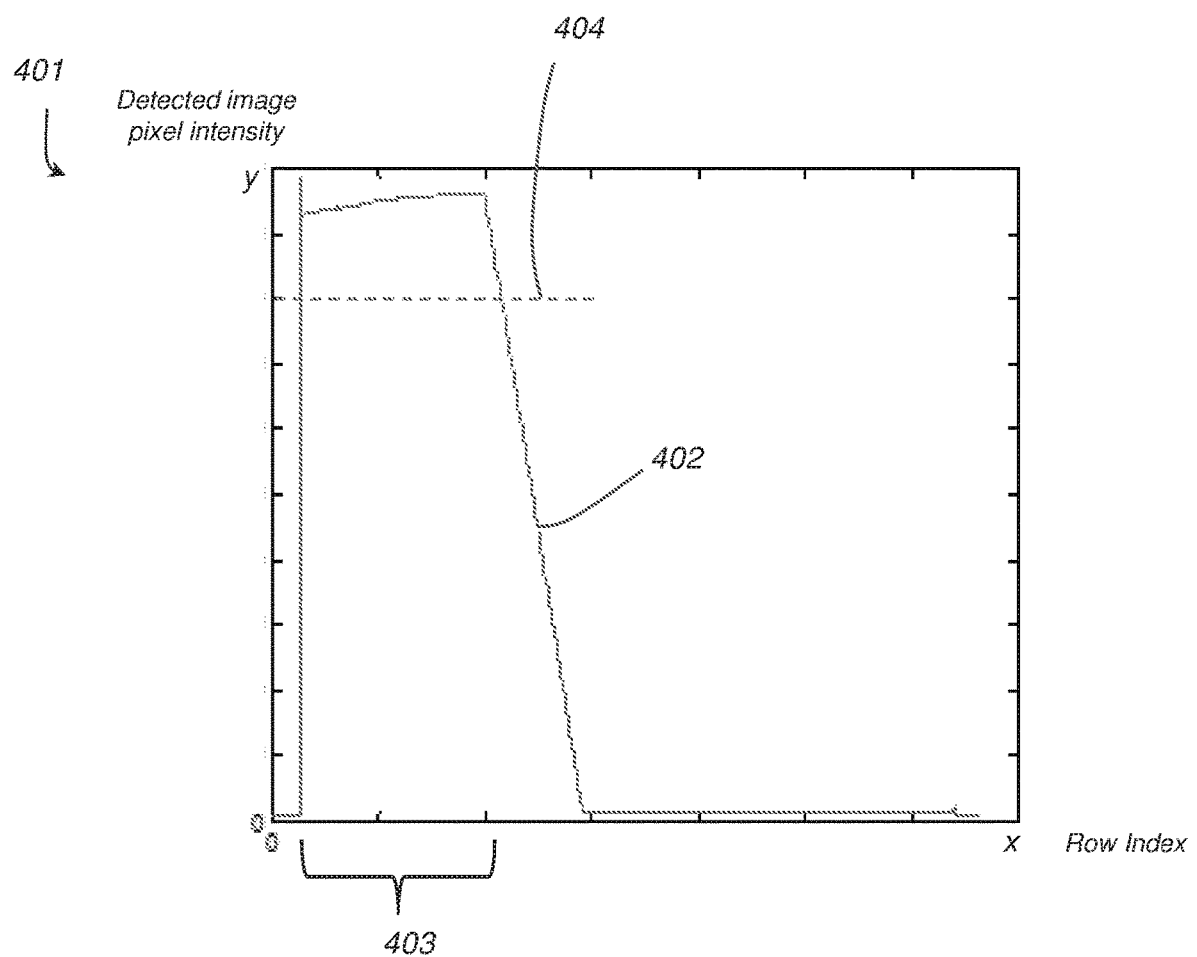
FIG. 4 is an exemplary graph of detected x-ray beam intensity across several rows of a detector's imaging pixel array.

With reference to FIG. 4, there is illustrated a representative graph 401 showing a plot of mean measured radiographic energy 402 per row of pixels in the detector 40. A portion of the detector's pixel rows 403 is exposed to an x-ray source and receives an amount of radiographic energy that exceeds a preset detector threshold 404. This pattern of pixel exposure may indicate that an activated x-ray source has been collimated to expose a portion of the imaging pixels in the detector 40 to the x-ray beam. As shown in FIG. 4, pixel rows nearest the top of the DR detector array are indexed closest to the origin (0, zero) along the horizontal x axis, while pixel rows nearest the bottom of the DR detector array are indexed further toward the right along the horizontal x axis. As shown in FIG. 4 the plot of mean detected x-ray beam intensity 402 does not exhibit negative (<0) values, as may be expected. However, noise sources are known to cause (oscillating) positive and negative going signals (e.g., FIG. 6) as detected at the array's read-out circuitry and so may be used as indicators of a false beam on detection. In one embodiment, negative going signals, or intensity values, detected at read-out integrated circuits (or ROICs) may be used to indicate that a noise event has occurred and not a beam-on event. A noise causing event may include physical impacts upon the detector, such as bumping, compressing, bending, etc., of the detector. Any of these, or similar noise generating events, such as thermal or magnetic field events may result in an oscillating signal, detected in the electronic read-out circuits of a DR detector, which have positive and negative going fluctuations. Methods of monitoring the array of imaging pixels in the detector to detect negative signals for verification of a false beam on event are described herein.

In one embodiment, a detector's imaging array and electronic circuits may be monitored and evaluated based on various design considerations. These may include required signal thresholds, duration of timing windows, and magnitude or amount of deviations or excursions from a preset value, as will be described herein. A detector's imaging array may be evaluated per designated sections of the array, which evaluations may be combined into a full image frame evaluation in order to determine how to disposition a full frame of image data. If the evaluation indicates that a noise event has been detected during a capture of a frame of image data, the design parameters may be consulted to determine how to disposition the full frame of image data. In one embodiment, it may be determined beforehand that a frame of image data will be discarded if a noise event has been detected and a beam-on event has not been detected. In one embodiment, it may be determined beforehand that a frame of image data will be saved as an offset image, or a correction image, if a noise even has not been detected and a beam-on event has not occurred. Two or more of such detected offset images may be detected and combined into one offset image; or a weighted average offset image may be calculated, using two or more of such offset images, and stored for image correction purposes. In one embodiment, it may be determined beforehand that a frame of image data will be saved as an exposure image (diagnostic) even if a noise event has been detected (or not), so long as a legitimate beam-on event has also occurred during a capture of such a frame of image data. These preselected disposition parameters may be embodied in on-board software that programmably controls image handling operations in the DR detector.

Figure 5:
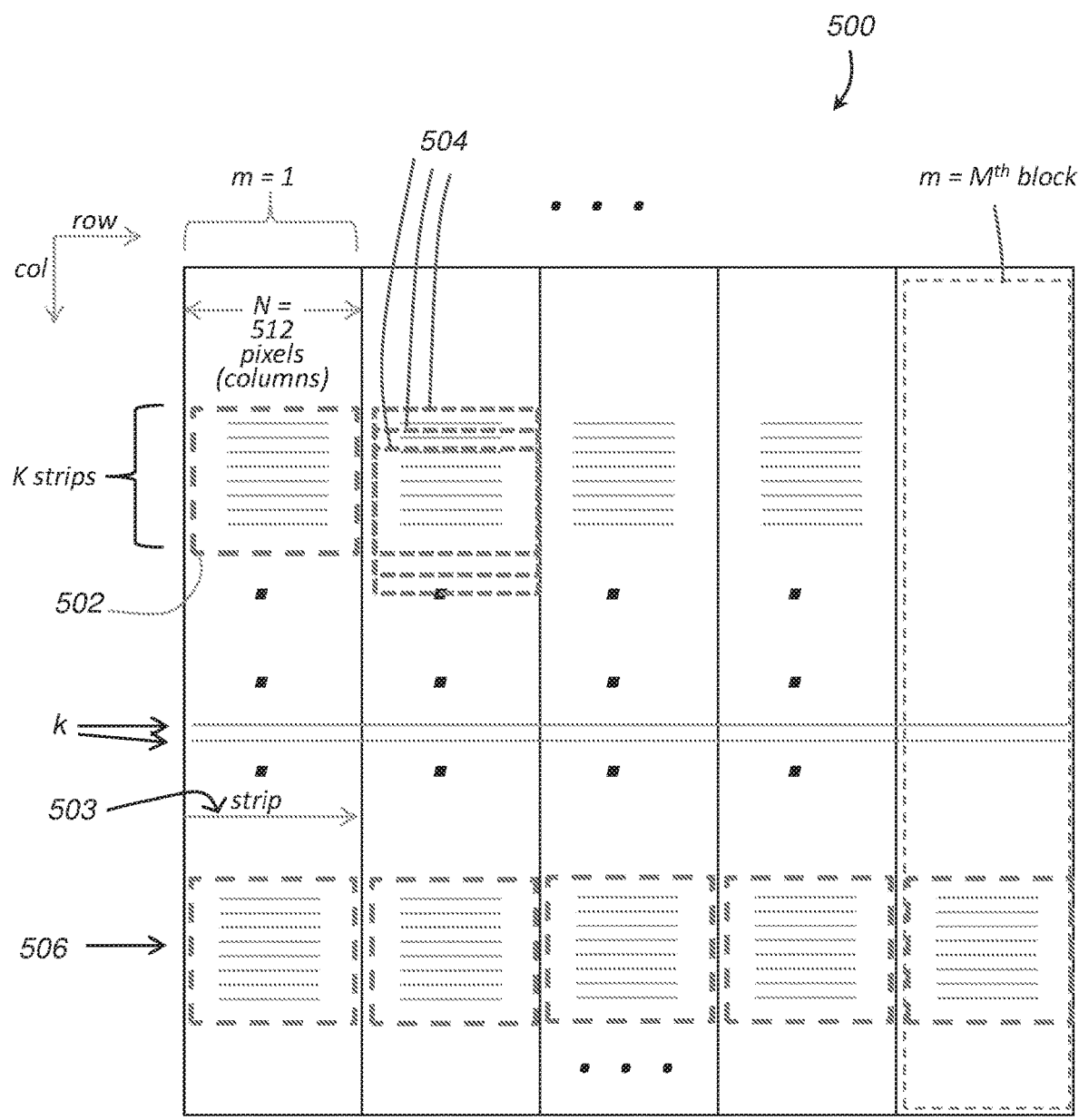
FIG. 5 is a schematic diagram of a pixel array illustrating exemplary logical operations of one embodiment of the present invention.

Referring to FIG. 5, there is depicted a representation of a detector's array of imaging pixels 500 divided into logically addressable portions that may be used for the pixel evaluations and image frame dispositions described herein. The array of imaging pixels 500 may be accessed for read out using pixel addressing per column and row. The entire array of imaging pixels 500, individual pixels, and subsets of pixels, such as blocks, strips, or windows, may be programmably addressed, accessed, read out, measured, evaluated, classified, stored, logically combined, and processed by column and row. As shown in FIG. 5, columns of pixels may be said to extend vertically and rows of pixels may be said to extend horizontally. To practice the methods described herein, the columns of pixels may be logically divided into M blocks m, where M=5, for example, and each block m includes N columns of pixels, which columns extend from a top of the array to a bottom of the array. In this exemplary embodiment, N=512 pixels, and so each imaging pixel row k may thereby be said to contain (5×512) total pixels based on N=512 columns for each of M=5 blocks. It should be noted that N and M values are arbitrary and may be chosen based on individual architecture design considerations. A "strip" 503 is defined herein as a portion of a row containing 512 consecutive pixels in a horizontal direction all in one of the M blocks. Thus, five consecutive horizontal strips in this example are equivalent to one entire row k. An exemplary "window" of pixels 502 may be defined to contain K consecutive strips of pixels in a vertical direction, where K may range from about 2 to about 128 to define a window size. Multiple overlapping windows 504 may be processed individually, as described herein. For image analysis purposes, i.e., beam-on verification, statistical measures may be computed and stored for each row k, window 502, strip 503, for five consecutive horizontal windows 506 across the detector, or for the entire array of the detector, i.e., a full image frame. Such statistical measures may include measures of centrality such as a median or mean. Although the rows k of pixels are illustrated in groups as multiple parallel lines in FIG. 5, such as in windows 502, 504, 506, it will be understood that the columns and rows of pixels extend continuously with substantially equal spacing along columns and rows, from top-to-bottom and side-to-side, respectively, in the detector. It will also be recognized that the portions formed as logical divisions of the detector array described herein, e.g., strips, windows and blocks, may contain any arbitrary amount of pixels.

The methods described herein may be useful to determine whether an x-ray beam, e.g., a "beam-on" event, impacting the pixels of the detector 500 has occurred by monitoring the detector's read-out circuitry for the presence of negative going signals. In one embodiment, the methods described herein may be useful to detect a collimated x-ray beam impacting the detector to capture a radiographic image of an object using only a fraction of the total number of pixels in the image frame of DR detector 500 due to the collimation. In order to detect an x-ray beam collimated onto a small area of the detector, which area may appear anywhere in the array of imaging pixels, the methods disclosed hereunder may be performed to process a portion, or the entire array, of imaging pixels. Thus, while the description hereunder may refer to processing a window 502 of imaging pixels, or consecutive horizontal windows 506 of imaging pixels, the method described herein may be performed such that all the imaging pixels in the DR detector 500 are thereby processed. In one embodiment, all the rows of the detector's imaging pixels are continuously processed frame by frame, even if a beam on event does not occur, according to the methods described herein, until a beam-on event is detected, whereafter the methods may be at least temporarily halted while further standard radiographic image capture processing continues in the detector and/or a beam off detection procedure is initiated.

In one exemplary embodiment of the methods disclosed herein, the detector read-out circuitry is monitored for negative going output signals after positive going output signals are detected. Such negative going signals are typically caused by noise sources, and may be identified by their positive-negative (+/−) oscillation. If such a negative signal is detected within a preset time window after a positive signal is detected, the positive signal detection may be programmably classified as a noise signal, or a non-x-ray signal, and may be ignored for the purpose of indicating a beam-on event (no legitimate x-ray beam-on detection). The usefulness of this method stems from the fact that x-rays impacting imaging pixels in the detector do not cause negative going oscillating signals in the detector circuitry.

Figure 6:
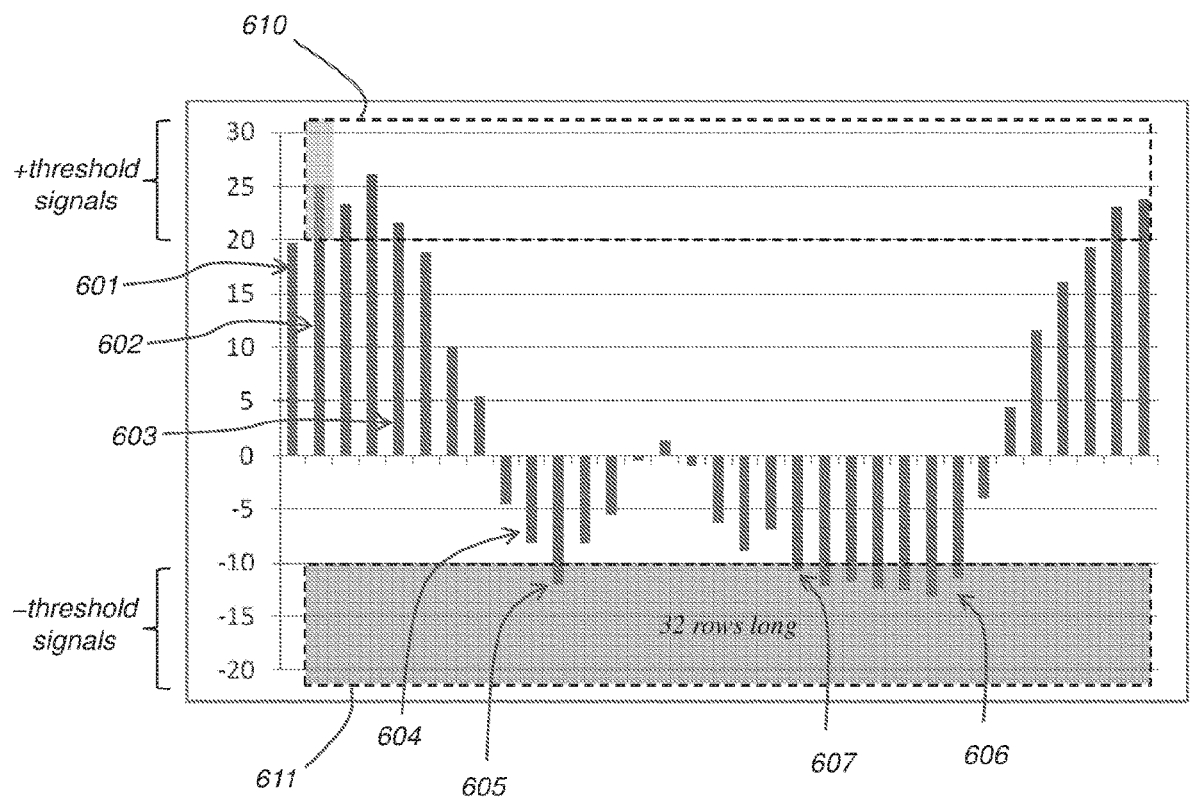
FIG. 6 is an exemplary diagram showing evaluation of an imaging array row by row.

With reference to FIG. 6, a programmed process for implementing one embodiment of the present invention will now be described. FIG. 6 may be said to illustrate a discrete representation of an oscillating signal detected in a DR detector as described herein. The bars in the graph of FIG. 6 each represent a mean, for example, of signal intensities for a strip of imaging pixels as detected at the outputs of the detector's readout circuitry. Moving from left-to-right in the graph of FIG. 6, each bar represents a measured mean of the next vertically downward consecutive strip in a sample window 502 of the array 500. Because the rows k of the array 500 are read out from left to right starting from the top and continuing toward the bottom, the bars in the graph of FIG. 6 are measured over substantially equal time intervals in the left-to-right direction.

A first exemplary positive signal intensity mean 601 detected in one strip of pixels of the array 500, as illustrated, does not reach a positive intensity +threshold, e.g., a preselected (preprogrammed) value of 20 as designated by the bottom border of the dashed line rectangle 610. The intensity value units (e.g. voltages) and thresholds may be arbitrarily chosen according to desired design considerations. In one embodiment, because the measured positive signal mean 601 does not reach the +threshold it may be ignored for purposes of classifying the positive signal mean 601 as a detected positive signal. As described herein, a positive signal mean above the +threshold is classified as a detected positive signal and may be used to start, i.e., be designated as a first strip, in a logically defined sample window 502. A next vertically consecutive strip of the array 500 is detected to have a positive signal mean 602 because it exceeds the preselected +threshold. In one embodiment, in order to start a logically defined and monitored sample window 502, a minimum preselected number of detected positive signals may be required, such as a number between one (1) and twelve (12), for example. The preselected count of detected positive signals may also be required to be consecutive signals or a cumulative number. If the +threshold required minimum number is preset at one (1), then the detection of the positive signal mean 602 will logically start a monitoring window. The monitoring window size is defined by a preselected number of vertically consecutive strips of pixels. The strips in this exemplary logically defined window are thereafter monitored to detect negative going signals therein.

In the example of FIG. 6, the window started by the one detected positive signal mean 602 is programmed, or preselected, at 32 strips, as depicted by the width of the dashed line rectangle 610. It should be noted that the 32-strip width of the dashed line rectangle 610 corresponds to a window 502, as illustrated in FIG. 5, where K=32. If the minimum preselected number of detected positive signals is preset at four (4) and is preset to be a consecutive detection instead of cumulative, for example, then the detection of four consecutive positive signal means (four vertically consecutive strips each having a pixel intensity mean exceeding the +threshold) logically starts a 32-row monitoring window, or sample window, that includes the first strip having a detected positive signal mean 602, the fourth consecutive strip having a detected positive signal mean 603, the two strips between them, and the twenty-eight strips following the strip having a detected positive signal mean 603. The threshold window 610 may be preset to include any number of strips of pixels at any preset+/−thresholds that are programmably set and monitored for positive and negative signals. If the negative signals, e.g., negative signal 605, are detected within the preset window size, the starting strip of the window in which the positive signal mean 602 was detected is classified as having been caused by a microphonic (μP) noise event and not an x-ray beam-on event. If no negative signals are detected in the pixel strips of the sample window, the strip in which the starting positive signal mean 602 was first detected is classified as having detected a legitimate x-ray beam-on event. The classifications for each strip so measured and evaluated are stored and used for row classification and image frame disposition, as described herein.

Continuing with the example of FIG. 6, a negative signal mean 604 may be detected in a subsequent strip of the detector array 500 within the 32-strip length sample window 610 started by the positive signal 602. In one embodiment, a preselected negative −threshold may be preset such that a magnitude of this negative signal mean 604 does not satisfy the −threshold, as indicated by the negative signal mean 604 not reaching top border of the −threshold window 611. For discussion purposes herein, the sample window 611 has the same width (number of strips) as sample window 610 so either window may be referenced herein for designating a sample window width, although the sample windows for positive and negative thresholds 610, 611, are not required to have the same width. In one embodiment, because the measured negative signal mean 604 does not reach the −threshold it may be ignored for purposes of classifying the negative signal mean 604 as a detected negative signal, and so is not used for purposes of verifying a beam-on event. A subsequent exemplary negative going signal 605 is detected in the array 500 within the 32-strip length sample window 611 started by the positive signal 602 which does satisfy the preset −threshold. If the −threshold required count is preset at one (1), then the detection of one consecutive negative signal 605 will result in a strip classification of the strip 602 as a noise detection, i.e., as having detected a μP noise event, and not a beam-on event. If the −threshold required count is preset at a number greater than one (1), for example, from two to twelve (2-12), and is preset as requiring consecutive detection, for example, then the detection of one consecutive negative signal 605 will not be sufficient to classify the positive signal mean measurement represented by strip 602 as a noise event. Instead, if a group of two or more, e.g., seven (7) consecutive signals 606, satisfying the −threshold are programmably preset, all occurring within the preset sample window, is required, whichever number is preset by program control, then the detection of seven consecutive negative signals 606 will result in a strip classification for strip 602 as having detected a μP noise event, and not a beam-on condition. If the −threshold required count is not preset for a consecutive detection. e.g., it is set for a cumulative detection of two, then the detection of the signal 605 will count as the first −threshold detection and the detection of the signal 607 will count as the second −threshold detection, satisfying the preset condition, and will result in a strip classification of strip 602 (the strip that detected positive signal 602) as having detected a P noise event, and not a beam-on condition.

The +threshold and −threshold detections are monitored and measured in the array of imaging pixels 500 using fixed preset processing window sizes 502 to process all the imaging pixels in the array 500. Row dispositions cover an entire row k in the array 500 and so require the results of horizontally consecutive window dispositions that all include the row being dispositioned. Thus, the row dispositions require processing coordination using the inputs from consecutive horizontal windows 506 that span the entire row and provide detection information for each portion of the row, i.e., each strip. In one embodiment, a positive signal mean for a particular strip in any of the windows 506 is logically ORed with the strips in other windows 506 corresponding to the particular row, so that a positive detection for a strip in one or more windows of the group of five windows 506 corresponding to a particular row will result in a positive detection classification for that particular row. This example is illustrated in FIG. 6, using, for example, the positive strip signal mean 602 that corresponds to a particular row k. In one embodiment, a preset number of strips in one row must be measured to have a positive signal mean to result in a positive detection classification for that particular row.

FIG. 7 illustrates exemplary tables of possible strip classifications, frame classifications, and frame dispositions that may be used in one embodiment of the present invention. With regard to the Strip Classification table of FIG. 7, strips are classified (third column) into one of three possible classes: Noise, Beam On, or Dark based on detected and averaged signal intensities per strip (first two columns) that fall within predesigned threshold conditions per window, as described herein, which threshold conditions may be based on detected and measured signal intensities, window length, and consecutive or non-consecutive strip requirements. The +Threshold Condition and −Threshold Condition results are shown in the first two columns of the Strip Classification table with resulting Strip Classification in the third column. The Strip Classification table of FIG. 7 indicates possible strip classifications resulting from the operations described herein in relation to FIG. 6. With regard to the first row of the Strip Classification table, a +threshold detection (preselected +threshold parameters satisfied) and a −threshold detection (preselected −threshold parameters satisfied) in a sample window 502 of the array 500 results in a programmed algorithm classifying the strip, strip 602 in the example of FIG. 6, as Noise—having detected a positive going signal event caused by noise. With regard to the second row of the Strip Classification table, a +threshold detection and no −threshold detection in a sample window 502 of the array 500 results in a programmed algorithm classifying the corresponding strip as Beam On—having detected a beam-on event. With regard to the third row of the Strip Classification table no +threshold detection and a −threshold detection in a sample window 502 of the array 500 results in a programmed algorithm classifying the corresponding strip as Noise—having detected a noise event. With regard to the fourth row of the Strip Classification table no +threshold detection and no −threshold detection in a sample window 502 of the array 500 results in a programmed algorithm classifying the corresponding strip as Dark. Strip classifications are electronically stored for later use in classifying frames and dispositioning image frames, as described herein.

With regard to the Frame Classification table of FIG. 7, frames are classified (third column) into one of three possible classes: Beam Detect. Noise, or Dark based on corresponding strip classifications from the Strip Classification table, as described herein. The possible Strip Classification table results are shown in the first two columns of the Frame Classification table with resulting frame classification in the third column. As used herein "frame", "image frame", and "array 500" may be used synonymously. With regard to the first row of the Frame Classification table of FIG. 7, a strip classification of Beam On (first column) in any one strip of the array 500 results in a programmed algorithm classifying the frame which contains the Beam On classified strip as Beam Detect even if any number of other strips in the array 500 were classified as Noise or Dark (second column). With regard to the second row of the Frame Classification table, the absence of a Beam On (first column) classification within any strip of the array 500, and having any strip of the array 500 classified as Noise (second column), results in a programmed algorithm classifying the frame as Noise. With regard to the third row of the Frame Classification table, the absence of a Beam On classification or Noise classification within any strip of the array 500, i.e., all strips are classified as Dark (first two columns), results in a programmed algorithm classifying the frame as Dark. Frame classifications are electronically stored for later use in dispositioning image frames.

The Current Frame Disposition table of FIG. 7 illustrates the final frame disposition (third column) of a frame being currently evaluated based on the Prior Frame Classification (first column), which is a classification of a frame immediately preceding the current frame being evaluated, and the Current Frame Classification (second column), which is a classification of the current frame being evaluated. The prior and current frame classifications are obtained from the Frame Classification table described above. As shown in the first row of the Current Frame Disposition table, a current image frame will have a frame disposition as Continue Radiographic Capture if the prior frame classification was Beam Detect and if the current frame classification is also Beam Detect. With this frame disposition, the detector is programmed to save the current frame as a diagnostic image frame for examination purposes and normal diagnostic radiographic image capture and processing according to the methods described, for example, in International Application WO 2016/094503 A1. With regard to the second row of the Current Frame Disposition table, a current image frame will be dispositioned as End Radiographic Capture if the prior frame classification is Beam Detect and if the current frame classification is not classified as Beam Detect. With this frame disposition, the detector is programmed to halt the classification and disposition process described herein, save the current frame as a diagnostic image frame for examination purposes where normal diagnostic radiographic image capture and processing may be performed by the detector according to the methods described, for example, in International Application WO 2016/094503 A1. As shown in the third row of the Current Frame Disposition table, a current image frame will be dispositioned as Start Radiographic Capture if the prior frame classification is not classified as Beam Detect and the current frame classification is Beam Detect. With this frame disposition, the detector is programmed to save the current frame as a diagnostic image frame for examination purposes and normal diagnostic radiographic image capture and processing according to the methods described, for example, in International Application WO 2016/094503 A1. As shown in the fourth row of the Current Frame Disposition table, a current image frame will be dispositioned as Discard if the prior frame classification is not Beam Detect and if the Current Frame Classification is Noise. With this frame disposition, the detector is programmed to discard the current frame being evaluated. As shown in the fifth row of the Current Frame Disposition table, a current image frame will be dispositioned as Capture Dark if the prior frame classification is not Beam Detect and the current frame classification is Dark. With this frame disposition, the detector is programmed to store the current image frame for later use for image correction purposes, such as for offset correction. Multiple dark image frames may be stored and combined for later use as image correction frames. These frames may be combined using an additive algorithm, a subtractive algorithm, or another suitable algorithm.

Figure 8:
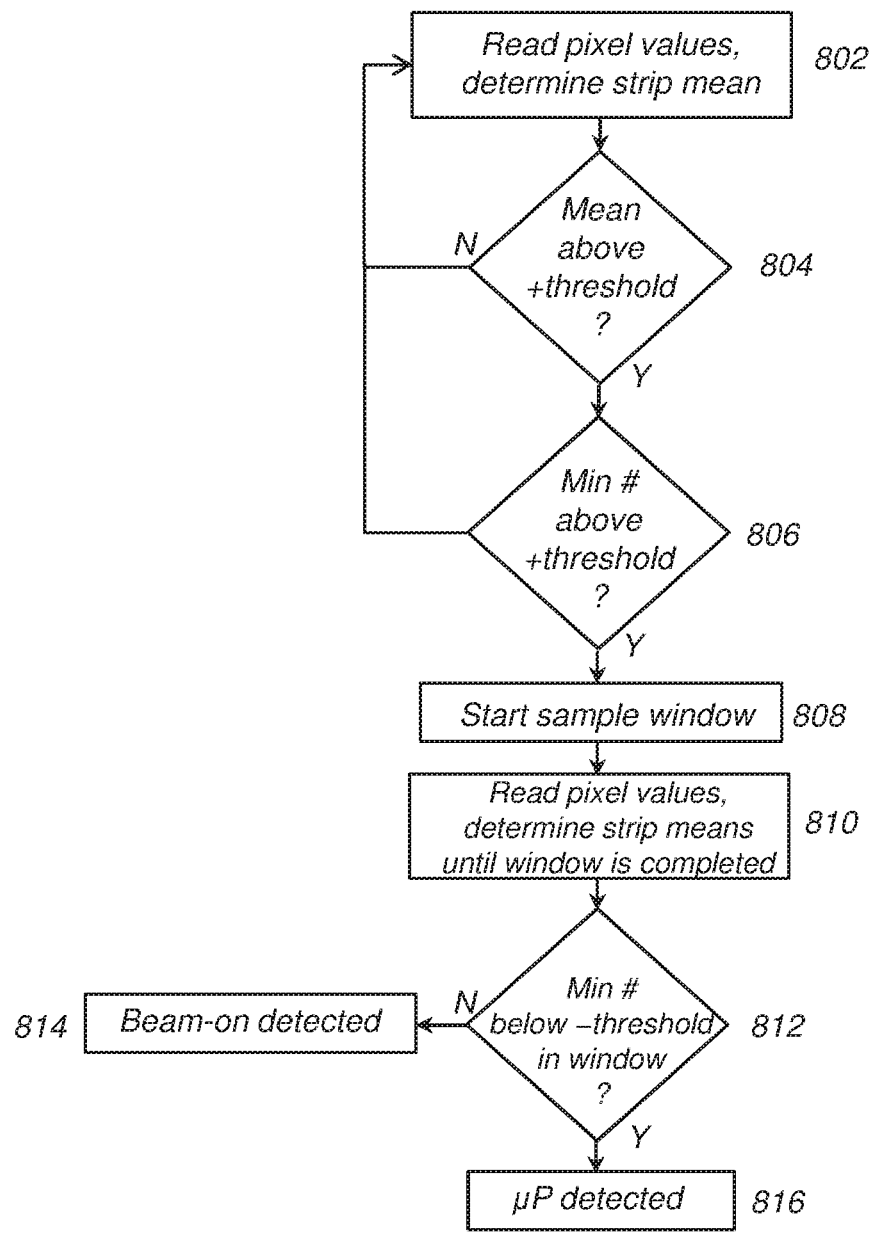
FIG. 8 is an exemplary flowchart of one embodiment of the present invention.

FIG. 8 is a flowchart illustrating one embodiment of a method of the present disclosure performed by a programmed processor controlling electronic operations of a DR detector. In step 802, a mean intensity value is determined for a number of pixels in a strip, and stored. In step 804, the determined mean intensity value is compared to a preselected stored +threshold, and if the determined mean intensity value is not above the +threshold it will not be counted as a positive +threshold detection, and the method proceeds back to step 802 to determine a strip mean intensity value of the next strip in a block. In step 804, if the determined mean intensity value is above the +threshold it will be counted as a positive +threshold detection and the method proceeds to step 806. To perform step 806, a preselected minimum number is stored which represents a minimum number of strips to be detected above the +threshold to result in a beam-on-to-be-verified event. In the example embodiment of FIG. 8, the minimum stored number is one (1) to demonstrate a simple example of the method. If the minimum number of strips needed to be measured above the +threshold is not satisfied at step 806, the method proceeds back to step 802 to determine a strip mean intensity value of the next strip in a block. If the minimum number of strips needed to be measured above the +threshold is satisfied at step 806, then in step 808, a sampling window having a preset size (number of strips) is initiated. The preset sampling window size is another value that is preselected and stored to be used in the method of FIG. 8. At step 810, the mean intensity values are determined for the number of strips defined by the preset sampling window size. To perform step 812, a preselected number representing a negative strip value −threshold is stored and used for comparison. The number of mean intensity values below the −threshold is determined for the evaluated strips in the defined sampling window at step 812. At step 812, if the number of strips in the sampling window does not satisfy the negative strip value −threshold, then the beam-on-to-be-verified event is indicated as a valid detection of a beam on, at step 814. At step 812, if the number of strips in the sampling window satisfies the negative strip value −threshold, then the beam-on-to-be-verified event is indicated as a noise event at step 816.

As will be appreciated by one skilled in the art, aspects of the present invention may be embodied as a system, method, or computer program product. Accordingly, aspects of the present invention may take the form of an entirely hard-coded hardware embodiment, an entirely software embodiment (including firmware, on-board resident software, micro-code, etc.), or an embodiment combining software and hardware aspects that may all generally be referred to herein as a "processor", "circuit," "circuitry," "module," "processing unit," and/or "processing system." Furthermore, aspects of the present invention may take the form of a computer program product embodied in one or more computer readable medium(s), such as electronic memory having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of operating a digital radiographic detector that includes a plurality of imaging pixels disposed in rows and columns, the method comprising:

monitoring an output signal from each of a plurality of individual adjacent strips of the imaging pixels of the detector, wherein the individual adjacent strips each consist of a preselected portion of one of a plurality of adjacent rows of the imaging pixels;

when detecting one or more only positive signals in the output signals that satisfy a preset positive threshold, determining that the detected one or more only positive signals are caused by x-rays impacting the imaging pixels; and when detecting one or more negative signals in the output signals that satisfy a preset negative threshold, determining that any detected positive signals are not caused by x-rays impacting the imaging pixels.

2. The method of claim 1, wherein the step of detecting one or more only positive signals further comprises:

measuring a magnitude of the detected one or more only positive signals; and determining that the magnitude of the detected one or more only positive signals satisfies the preset positive threshold.

3. The method of claim 2, further comprising:

determining a number of the detected one or more only positive signals whose magnitude satisfies the preset positive threshold; and determining that the number of the detected one or more only positive signals whose magnitude satisfies the preset positive threshold also satisfies a preset number threshold.

4. The method of claim 2, wherein the step of measuring further comprises determining a statistical measure of the magnitude of the detected one or more only positive signals.

5. The method of claim 1, further comprising:

capturing radiographic image data in the detector; and storing the captured radiographic image data for diagnostic purposes based upon the step of determining that the detected one or more only positive signals are caused by x-rays impacting the imaging pixels.

6. A method of operating a digital radiographic detector that includes a plurality of imaging pixels disposed in rows and columns, the method comprising:

monitoring output signals from each of a plurality of individual adjacent strips of the imaging pixels of the detector, wherein the individual adjacent strips each consist of a preselected portion of one of a plurality of adjacent rows of the imaging pixels;

when detecting only positive signals in the output signals that satisfy a preset positive threshold, determining that the detected positive signals are caused by x-rays impacting the imaging pixels; and when detecting negative signals in the output signals that satisfy a preset negative threshold, determining that any detected positive signals are not caused by x-rays impacting the imaging pixels.

7. The method of claim 6, wherein the step of detecting negative signals further comprises:

measuring a magnitude of the detected negative signals; and determining that the magnitude of the detected negative signals are greater than a preset negative threshold.

8. The method of claim 7, further comprising:

determining a number of the detected negative signals whose magnitude are greater than the preset negative threshold; and determining that the number of the detected negative signals whose magnitude are greater than the preset negative threshold also satisfy a preset number threshold.

9. The method of claim 7, wherein the step of measuring further comprises determining a statistical measure of the magnitude of the detected negative signals.

10. The method of claim 6, further comprising:

capturing a frame of radiographic image data in the detector; and discarding the frame of radiographic image data based upon the step of determining that any detected positive signals are not caused by x-rays impacting the imaging pixels.

11. A method of operating a digital radiographic detector that includes a plurality of imaging pixels disposed in rows and columns, the method comprising:

monitoring output signals from a plurality of imaging pixel windows, wherein the imaging pixel windows each consist of a portion of each of two or more adjacent rows of the imaging pixels;

when detecting only positive signals in the output signals that satisfy a preset positive threshold, determining that the detected only positive signals are caused by x-rays impacting the imaging pixels; and when detecting negative signals in the output signals that satisfy a preset negative threshold, determining that any detected positive signals are not caused by x-rays impacting the imaging pixels.

12. The method of claim 11, wherein the step of detecting negative signals further comprises:

measuring a magnitude of the detected negative signals; and determining that the magnitude of the detected negative signals are greater than a preset negative threshold.

13. The method of claim 12, further comprising:

determining a number of the detected negative signals whose magnitude are greater than the preset negative threshold; and determining that the number of the detected negative signals whose magnitude are greater than the preset negative threshold also satisfy a preset number threshold.

14. The method of claim 12, wherein the step of measuring further comprises determining a statistical measure of the magnitude of the detected negative signals.

15. The method of claim 11, further comprising:

capturing a frame of radiographic image data in the detector; and discarding the frame of radiographic image data based upon the step of determining that any detected positive signals are not caused by x-rays impacting the imaging pixels.

16. The method of claim 11, wherein the step of detecting only positive signals further comprises:

measuring a magnitude of the detected only positive signals; and determining that the magnitude of the detected only positive signals satisfies the preset positive threshold.

17. The method of claim 16, further comprising:

determining a number of the detected only positive signals whose magnitude satisfies the preset positive threshold; and determining that the number of the detected only positive signals whose magnitude satisfies the preset positive threshold also satisfies a preset number threshold.

18. The method of claim 16, wherein the step of measuring further comprises determining a statistical measure of the magnitude of the detected only positive signals.

19. The method of claim 11, further comprising:
   capturing radiographic image data in the detector; and
   storing the captured radiographic image data for diagnostic purposes based upon the step of determining that the detected only positive signals are caused by x-rays impacting the imaging pixels.

* * * * *